United States Patent [19]
Lahanas et al.

[11] Patent Number: 6,042,839
[45] Date of Patent: Mar. 28, 2000

[54] POWDER COMPOSITIONS

[75] Inventors: Konstantinos M. Lahanas, Paramus, N.J.; Tracy N. Keeler, East Northport; Daniela Toma, Floral Park, both of N.Y.

[73] Assignee: Color Access, Inc., Melville, N.Y.

[21] Appl. No.: 09/036,734

[22] Filed: Mar. 9, 1998

[51] Int. Cl.⁷ .............................. A61K 6/00; A61K 9/14; A61K 7/035

[52] U.S. Cl. ......................... 424/401; 424/489; 424/464; 424/465; 424/488; 424/490; 424/78.02; 424/69

[58] Field of Search ...................... 424/489, 464, 424/465, 488, 490, 78.02, 401, 69

[56] References Cited

U.S. PATENT DOCUMENTS 5,144,016  9/1992  Skjak-Braek et al. .
5,622,693  4/1997  Funatsu .

FOREIGN PATENT DOCUMENTS

| | | |
|---|---|---|
| 315541 | 5/1989 | European Pat. Off. . |
| 2498451 | 7/1982 | France . |
| 2 729 568 | 7/1996 | France . |
| 61-017506 | 1/1986 | Japan . |
| 63 037156 | 8/1986 | Japan . |
| 63-130522 | 6/1988 | Japan . |
| 5-247435 | 9/1993 | Japan . |
| 761 757 | 11/1956 | United Kingdom . |
| 2 226 039 | 6/1990 | United Kingdom . |
| WO 93 07855 | 4/1993 | WIPO . |

*Primary Examiner*—Thurman K. Page
*Assistant Examiner*—Todd D Ware
*Attorney, Agent, or Firm*—Kenyon & Kenyon

[57] ABSTRACT

The present invention relates to cosmetic or pharmaceutical compositions comprising a powder containing a water soluble carboxylated gum and a clay crosslinked with metal ions.

31 Claims, No Drawings

POWDER COMPOSITIONS

FIELD OF THE INVENTION

The invention relates to cosmetic compositions. More particularly, the invention relates to powder-containing cosmetic compositions.

BACKGROUND OF THE INVENTION

Powders are a very common component of a wide variety of cosmetics. They serve a number of purposes in such compositions: they can be used as binders, to hold other components together; as fillers, to give greater substance to a product; as oil removers, as in facial powders, to absorb oils and sebum from the face; and water absorbers, to dry the skin after a shower or a bath. There is a vast array of different types of powders, each of which may perform one or more of the desired functions. Examples of commonly used powders are talc, kaolin, polystyrene, nylon, mica, starch, silica, and silk. However, the features which allow them to perform the noted functions may actually in some situations be disadvantageous. For example, many powders are so good at absorbing water, that they eventually dry out the skin too much. Also, it is preferred that a powder be light and fluffy, i.e., "powdery", rather than heavy and draggy, to the touch; however, in many cases, powders will pack tightly when settled or in the presence of water, thereby eventually losing the desirable powdery feel. In addition, powders are frequently unsuitable for the incorporation of biologically active materials, due to unfavorable interactions, such as oxidation, reduction, or hydrolysis. Therefore, there continues to be a need for a cosmetically acceptable powder which is light and non-drying, which can readily be used to deliver actives, and yet which can function as well as traditional powders in the ability to absorb oil and water. The present invention now provides such a powder.

SUMMARY OF THE INVENTION

The present invention relates to a hydrated powder comprising a water soluble carboxylated gum and a clay, crosslinked by metal ions. The powder may also comprise a pigment, to provide an additional desirable visual effect. The powder so prepared is light, fluffy, and highly oil- and water-absorbent. The invention also relates to a method of preparing a hydrated powder which comprises blending an aqueous dispersion or solution of the gum with the clay, adding a solution of metal ions until the mixture gels, and grinding the mixture to the desired size. The powder can be used directly as a slurry, or can be further dried to remove most of the water contained therein.

The powder prepared according to the present invention can be used in a variety of different cosmetic and/or pharmaceutical products. In one preferred embodiment, the product is a dual phase skin toner.

DETAILED DESCRIPTION OF THE INVENTION

The powder of the invention is relatively easily prepared. First, an aqueous solution or suspension of the water soluble carboxylated gum is blended to homogeneity with an aqueous dispersion of a clay. The gum can be any cosmetically or pharmaceutically acceptable gum, generally an anionic gum which is crosslinkable in the presence of metal ions. Examples of such gums include alginates, methyl-, hydroxyethyl- or carboxymethyl cellulose, carrageenan, guar gum, xanthan gum and the like. Particularly preferred are gums of alginic acid, and appropriate metal salts thereof, for example sodium or calcium alginate.

The clay to be used can be any cosmetically or pharmaceutically acceptable clay, either natural or synthetic. Examples of clays which can be used include, but are not limited to, hectorites, bentonites, montmorillonites, kaolin, fullers earth, and diatomaceous earth. A particularly preferred clay is Laponite, which is a synthetic smectic clay of the hectorite type structure,(manufactured by LaPorte, and distributed by RTD Chemicals). The CTFA or INCI name is sodium magnesium silicate.

A solution containing metal ions is added to the mixture to attain the desired crosslinking of the gum. Examples of useful sources of such metal ions include, but are not limited to, strongly electrolytic cosmetically or pharmaceutically acceptable acid salts of di- or trivalent metals, such as $Ca^{+2}$, $Al^{+2}$, $Fe^{+2}$, $Fe^{+2}$, $Cu^{+2}$, or $Mn^{+2}$.

The proportions in which the components are added are not critical. However, an effective combination results from the use of a gum in a range of, in dry weight, from about 0.01:1 to 10:1 relative to the amount of clay, with an excess of metal ions used. Although not essential to achieving crosslinking, the excess of metal ions does serve to prevent subsequent swelling of the composite in a fluid environment. The combined components are left for a period of time sufficient to permit gelling of the gum, which, under optimum conditions of concentration, and absence of inhibitors, is typically no more than a minute or so. The mixture at this point is quite thick, and before use, requires some further processing. In order to achieve the desired consistency, the gelled product is ground or milled, by simple homogenizing, to a particle size consistent with retention of a powdery texture. Generally, this will be in the range of 0.05–300 $\mu$m, more commonly in the range of 0.2–200 $\mu$m, and preferably in the range of from about 1–100 $\mu$m. The powder can then be used as is, i.e., as a slurry of small solid particles in fluid suspension, or it can be further air- or spray dried. The choice of further processing will depend upon its intended end use. In suspension, the powder is light and fluffy, spreading homogeneously and elegantly through the fluid environment upon agitation, but settling out completely and rapidly, i.e., with 24 hours, to a discrete powdery layer.

In a particularly preferred embodiment, to enhance the appearance of the resulting powder, a pigment is added to the mixture to be gelled. The pigment can be any inorganic or organic pigment which is insoluble in water. Examples of useful inorganic pigments include iron oxides (yellow, red, brown or black), ferric ammonium ferrocyanide(blue), manganese violet, ultramarine blue, chrome oxide(green), talc, lecithin modified talc, zeolite, kaolin, lecithin modified kaolin, titanium dioxide(white) and mixtures thereof. Other useful pigments are pearlants such as mica, bismuth oxychloride and treated micas, such as titanated micas and lecithin modified micas.

The organic pigments include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Particularly preferred lakes are primary FD&C or D&C lakes and blends thereof.

Also included are copolymer pigments that are water insoluble, e.g., nylon powder, polyethylene, and polyesters.

The polyesters can include linear, thermoplastic, crystalline or amorphous materials produced using one or more diols and one or more dicarboxylic acids copolymerized with colorants. Other pigments to be used in the invention will be apparent to one of ordinary skill in the art.

A particularly attractive powder is formed when the pigment employed is a pearlant such as mica. When a pigment is to be incorporated into the powder, it is first blended to homogeneity directly with the gum suspension, prior to addition to the clay component.

Additional components can also be added to the powder composition of the invention. As noted above, an advantage of the present powder is the ability to easily incorporate actives into the mixture. The active is essentially entrapped within the powder particles, which comprise an outer layer of alginate and an inner layer of clay. Any active can be employed in the composition, for example, Vitamin E and derivatives, Vitamin C and derivatives, Vitamin A and derivatives, antioxidants, emollients such as petrolatum or dimethicone, alpha- or beta-hydroxy acids, ceramides, or skin lipids to enhance barrier function. Other actives for topical application can be chosen from analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antiasthmatic agents and bronchodilators, sunscreen agents, antihistamine agents, skin lightening agents, depigmenting agents, wound-healing agents, vitamins, corticosteroids, tanning agents, or hormones. In preparation of the product, any actives to be used will preferably be dissolved or dispersed in the gum phase.

In combining other elements with the powder to achieve a final product, either before or after crosslinking occurs, care should be taken to avoid the presence of materials which will tend to de-crosslink the metal component, i.e., metal-complexing or chelating agents. If the presence of such a material is desirable, e.g., a salicylic acid component, it should be precomplexed with an appropriate metal before addition to the powder. Alternately, crosslinking can be performed with large excess of metal ions, which will leave additional ions unoccupied so that any complexing which does occur will not harm the integrity of the crosslinked product.

The powder of the invention is useful in a wide variety of cosmetic and pharmaceutical products, i.e., any type of product in which a powder component is desirable. Thus, the powder, in substantially dried form, can be the primary component of a facial or body powder, blush, eyeshadow, eyeliner, bath grains, or pellets, lipsticks, hair products and the like, particularly in products in which the additional function of oil control is desired. It can also be added, in dried or slurry form, to the aqueous phase of any water-containing makeup product, or alternately emulsified or otherwise suspended therein.

In a preferred embodiment, the powder is a component of a dual phase(liquid/solid) toner composition. The liquid portion of the toner comprises an aqueous base with astringent components, such as alcohol and/or witch hazel. Additional components depend upon the intended use of the toner, i.e., whether for dry or oily skin. Examples of useful actives may include exfoliating agents, either physical or chemical, antiirritants. Because of its velvety texture and non-drying properties, the powder of the invention is suitable for either type of toner. However, by virtue of its exceptional ability to absorb oil, is particularly well adapted for use in a normal-to-oily skin toner. The presence of a pigment in the powder adds a particularly attractive, decorative 'swirling' aspect to the solid phase of the composition.

The invention is further illustrated by the following non-limiting examples.

EXAMPLE I

EXAMPLES
This example illustrates the preparation of a powder according to the invention:

| Material | % by weight |
|---|---|
| Phase I | |
| Water | 67.00 |
| Disodium EDTA | 0.05 |
| Phase II | |
| Laponite XLS | 3.50 |
| Phase III | |
| Water | 7.75 |
| sodium alginate | 0.20 |
| Phase IV | |
| Mearlmaid AA* | 6.50 |
| Phase V | |
| water | 14.00 |
| cupric sulfate pentahydrate | 1.00 |

*water/guanine/isopropyl alcohol/methylcellulose (Mearl)

Phase I components are added to a kettle under low homomixer agitation. Phase II is added to Phase I under the same agitation, while heating to 70° C. The heat is maintained until no discrete particles are present, and the mixture cooled to 30° C.

The Phase III water is added to a separate kettle, and agitated at 150 rpm. The sodium alginate is added under the same agitation and the mixture is heated to 70° C.; mixing continues until the batch is smooth and then cooled to 30° C. At that point, the Phase 4 material is added under 150–200 rpm agitation, and mixed until homogeneity.

When homogeneous, the combined Phase III and IV materials are added to the Phase I and II materials under agitation and mixed until homogeneous. In a separate kettle, the Phase V ingredients are combined under 150 rpm agitation, and mixed until no discrete particles are visible. The Phase V ingredients are then added to the primary kettle at 150 rpm and blended until homogeneous; the batch at this stage becomes quite thick. Once it is homogeneous, mixing continues for an additional 30 minutes, until the batch is smooth. The mixture is ground to a particle size range of between 1–100 $\mu$m to create a slurry.

EXAMPLE II

A toner is prepared, using the powder of Example I, as follows:

| Material | % by weight |
|---|---|
| Phase I | |
| Water | 52.00 |
| 1,3-Butylene glycol | 12.00 |
| Aluminum chlorhydrate | 0.30 |

EXAMPLE II-continued

A toner is prepared, using the powder of Example I, as follows:

| Material | % by weight |
|---|---|
| Phase II | |
| Ethanol (200 proof) | 30.00 |
| Salicylic acid powder | 0.50 |
| Phase III | |
| Algae extract | 0.20 |
| Phase IV | |
| Powder of Example I (solids between 0.1–99% solids) | 5.00 |

Phase I materials are added sequentially to a primary kettle under 150–200 rpm agitation, and mixed until clear and no particles are visible.

In a second kettle, Phase II ingredients are added under 100–150 rpm agitation, and also mixed until clear. The Phase II material is then added to the primary kettle under 100–150 rpm agitation, and mixed until clear. Phase III is added and mixed until completely dissolved; the mixture is then filtered to remove any gross particles.

The filtered mixture is added back to the primary kettle, and Phase IV is added to it under 200–250 rpm agitation, mixed until homogeneous, and then passed through a colloid mill.

What we claim is:

1. A cosmetic or pharmaceutical composition comprising a powder containing a water soluble carboxylated gum and a clay crosslinked with metal ions.

2. The composition of claim 1 which also comprises at least one pigment.

3. The composition of claim 1 in which the gum is alginic acid or a derivative salt.

4. The composition of claim 1 in which the clay is selected from the group consisting of hectorites, bentonites, montmorillonite, kaolin, fullers earth, and diatomaceous earth.

5. The composition of claim 1 in which the metal is selected from the group consisting of cosmetically or pharmaceutically acceptable acid salts of di- or trivalent metals.

6. The composition of claim 5 in which the metal is selected from the group consisting of $Ca^{+2}$, $Al^{+2}$, $Fe^{+2}$, $Fe^{+2}$, $Cu^{+2}$, or $Mn^{+2}$.

7. A cosmetic or pharmaceutical composition comprising an aqueous slurry of a powder particles containing a water soluble carboxylated gum and a clay crosslinked with metal ions.

8. The composition of claim 7 in which the particle comprises an outer layer of gum and an inner layer of clay.

9. The composition of claim 8 which also comprises a pigment.

10. The composition of claim 7 in which the gum is an alginic acid or a derivative salt.

11. The composition of claim 7 in which the clay is selected from the group consisting of hectorites, bentonites, montmorillonite, kaolin, fullers earth, and diatomaceous earth.

12. The composition of claim 7 in which the metal is selected from the group consisting of cosmetically or pharmaceutically acceptable acid salts of di- or trivalent metals.

13. The composition of claim 7 which comprises an alginate gum and a Laponite crosslinked with metal ions.

14. The composition of claim 13 in which the powder further comprises a pigment.

15. The composition of claim 14 in which the powder further comprises a pearlescent pigment.

16. The composition of claim 8 in which the powder particle comprises an outer layer of alginate gum, and inner layers of Laponite and pearlescent pigment.

17. A method for preparing a powder composition comprising crosslinking (a) an aqueous suspension of a carboxylated gum with (b) an aqueous dispersion of a clay, in the presence of metal ions; and grinding the crosslinked composition to a powder consistency.

18. The method of claim 17 in which crosslinking is achieved in the presence of an excess of metal ions.

19. The method of claim 18 in which the gum is alginic acid or a derivative salt, the clay is selected from the group consisting of hectorites, bentonites, montmorillonite, kaolin, fullers earth, and diatomaceous earth, and the metal is selected from the group consisting of cosmetically or pharmaceutically acceptable acid salts of di- or trivalent metals.

20. The method of claim 19 in which the gum is sodium alginate, and the clay is Laponite.

21. A cosmetic or pharmaceutical composition prepared according to the method of claim 17.

22. A cosmetic or pharmaceutical composition prepared according to the method of claim 18.

23. A cosmetic or pharmaceutical composition prepared according to the method of claim 19.

24. A cosmetic or pharmaceutical composition prepared according to the method of claim 20.

25. A cosmetic composition having separate liquid and solid phases, in which the solid phase contains a powder comprising a water soluble carboxylated gum and a clay crosslinked with metal ions.

26. The composition of claim 25 in which the gum is an alginic acid or derivative salt, and the clay is selected from the group consisting of hectorites, bentonites, montmorillonite, kaolin, fullers earth, and diatomaceous earth, and the metal is selected from the group consisting of cosmetically or pharmaceutically acceptable acid salts of di- or trivalent metals.

27. The composition of claim 26 which also comprises a pigment.

28. The composition of claim 27 in which the liquid phase is aqueous, the gum is an alginate, and the clay is Laponite.

29. The composition of claim 28 in which the gum is sodium alginate, the clay is Laponite, and the pigment is a pearlescent pigment.

30. The composition of claim 25 which is a toner.

31. The composition of claim 30 which comprises an aqueous phase comprising at least one astringent, and a solid powder phase comprising a crosslinked alginate, Laponite and pigment.

* * * * *